United States Patent [19]

Braig et al.

[11] Patent Number: 4,894,091

[45] Date of Patent: Jan. 16, 1990

[54] PHENOLIC BENZOTHIAZOLE DERIVATIVES AND THEIR USE AS CORROSION INHIBITORS

[75] Inventors: Adalbert Braig, Weil-Friedlingen, Fed. Rep. of Germany; Hans-Rudolf Meier; David G. Leppard, both of Marly, Switzerland; Robert C. Wasson; Emyr Phillips, both of Cheshire, England

[73] Assignee: Ciba-Geigy Corporation, Ardsley, N.Y.

[21] Appl. No.: 86,337

[22] Filed: Aug. 17, 1987

[30] Foreign Application Priority Data

Aug. 27, 1986 [GB] United Kingdom ............... 8620668

[51] Int. Cl.$^4$ ................................................ C04B 9/02
[52] U.S. Cl. ............................... 106/14.16; 106/14.37; 106/14.38; 252/391
[58] Field of Search ............... 106/14.16, 14.37, 14.38; 252/391

[56] References Cited

U.S. PATENT DOCUMENTS

| | | |
|---|---|---|
| 3,215,641 | 11/1965 | Rocklin et al. |
| 3,219,701 | 11/1965 | O'Shea |
| 3,281,473 | 10/1966 | O'Shea |
| 3,291,841 | 12/1966 | O'Shea |
| 3,310,524 | 3/1967 | Hurlock et al. |
| 4,329,381 | 5/1982 | Eschwey et al. |
| 4,357,396 | 11/1982 | Grunewalder et al. ......... 106/14.38 |
| 4,696,763 | 9/1987 | Bently et al. .................... 106/14.16 |

FOREIGN PATENT DOCUMENTS

0003817 2/1981 European Pat. Off.
129506 12/1984 European Pat. Off.

OTHER PUBLICATIONS

C.A., 102, 149260s, (1985).
C.A., 91, 212415t, (1979).
C.A., 98, 145110u, (1983).
Derwent Abstract 85-220498/36.
E. M. Bickoff et al., J. Am. Oil Chem. Soc. 32, 64(1955).
Chem. Abst., 83, 9878p, (1975).
Derwent Abst. 83-40141k.

*Primary Examiner*—Jacqueline V. Howard
*Attorney, Agent, or Firm*—Luther A. R. Hall

[57] ABSTRACT

Compounds of the formula I

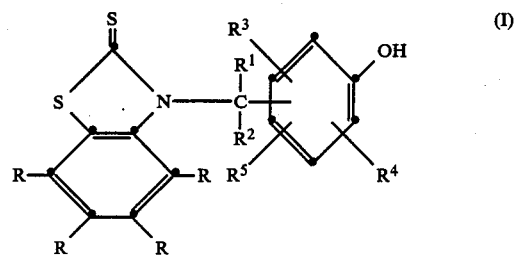

wherein R, $R^1$, $R^2$, $R^3$, $R^4$ and $R^5$ have the meaning given in claim 1 are formed by thermal rearrangement of the isomers of formula V

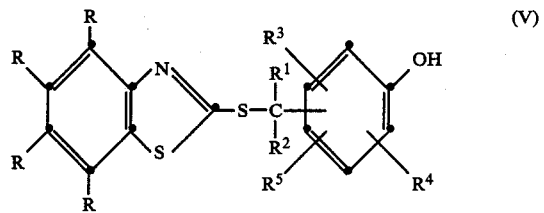

especially in the presence of basic catalysts. The compounds are corrosion inhibitors for organic materials, in particular coating materials and lubricants. In these substrates they also act as antioxidants and light-stabilizers and are very stable to heat.

19 Claims, No Drawings

PHENOLIC BENZOTHIAZOLE DERIVATIVES AND THEIR USE AS CORROSION INHIBITORS

The invention relates to phenolic derivatives of benzothiazole and to their use as corrosion inhibitors in organic materials, especially coating materials and lubricants.

Mercaptobenzothiazole and its salts are disclosed as corrosion inhibitors, for example in EP-A 3817. Various derivatives of mercaptobenzothiazole have also already been suggested as corrosion inhibitors, for example the benzothiazole-2-ylthiocarboxylic acids and their salts which are described in EP-A 129,506. These are predominantly derivatives containing hydrophilic groups.

It has now been found that certain benzothiazole derivatives containing hydrophobic groups can also be excellent corrosion inhibitors. These compounds additionally show an antioxidative and light-stabilizing activity. They can therefore be used as additives for organic materials in which inhibition of corrosion and/or stabilization against oxidation or against UV-light are desired. This is particularly the case with coating materials and lubricants.

Compared with known corrosion inhibitors based on benzothiazole derivatives, the compounds are distinguished by a lower water absorption, by chemical inertness and by a high stability to heat.

The invention relates in particular to compositions of a coating material or lubricant containing at least one compound of the formula I.

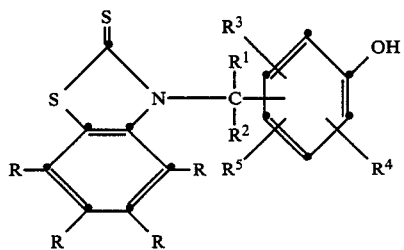

in which each R independently of one another is hydrogen, $C_1$–$C_{12}$-alkyl, $C_1$–$C_4$-halogenoalkyl, $C_1$–$C_{12}$alkoxy, $C_1$–$C_{12}$-alkylthio, phenylthio, benzylthio, $C_1$–$C_{12}$-alkylsulfonyl, phenyl, $C_7$–$C_{15}$-alkylphenyl, $C_7$–$C_{10}$-phenylalkyl, $C_5$–$C_8$-cycloalkyl, halogen, —$NO_2$, —CN, —COOH, —COO—($C_1$–$C_4$-alkyl), —OH, —$NH_2$, —$NHR^6$, —$N(R^6)_2$, —$CONH_2$, —$CONHR^6$ or —$CON(R^6)_2$, $R^1$ is hydrogen, $C_1$–$C_{12}$-alkyl, phenyl, phenyl which is substituted by halogen, $C_1$–$C_4$-alkyl, $C_1$–$C_4$-alkoxy or —$NO_2$, pyridyl, thienyl or furyl, $R^2$ is hydrogen or $C_1$–$C_4$-alkyl, $R^3$ and $R^4$ independently of one another are hydrogen, halogen, $C_1$–$C_4$-alkoxy, cyano, nitro, $C_1$–$C_{20}$-alkyl, —$(CH_2)_m$—$COOR^7$, —$(CH_2)_m$—$CONHR^6$, —$(CH_2)_m$—$CON(R^6)_2$, $C_3$–$C_{20}$-alkenyl, $C_7$–$C_{10}$-phenylalkyl, phenyl, cyclohexyl, cyclopentyl or a group of the formula II

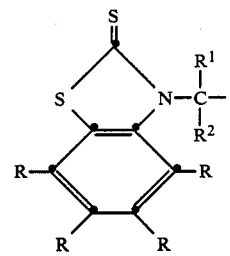

$R^4$ is hydrogen, $C_1$–$C_{20}$-alkyl, $C_3$–$C_{20}$-alkenyl or hydroxy, or $R^3$ and $R^5$ together or $R^4$ and $R^5$ together form a ring fused to the phenolic moiety which ring may be a carbocyclic or heterocyclic ring containing oxygen, nitrogen or sulfur as heteroatoms, each ring being optionally substituted by $C_1$–$C_4$-alkyl, $C_1$–$C_4$-alkoxy or halogen, $R^6$ is $C_1$–$C_{12}$-alkyl, $C_3$–$C_{12}$-alkyl which is interrupted by one or more O atoms, $C_5$–$C_8$-cycloalkyl, benzyl, phenyl or phenyl which is substituted by halogen, $C_1$–$C_4$-alkyl, $C_1$–$C_4$-alkoxy ot nitro, or —$N(R^6)_2$ is a pyrrolidino, piperidino or morpholino group, $R^7$ is hydrogen or $C_1$–$C_{20}$-alkyl, which may be substituted by halogen or hydroxyl or $R^7$ is $C_3$–$C_{20}$-alkyl which is interrupted by one or more oxygen atoms and may be substituted by hydroxyl and m is 0, 1 or 2.

In formula I, R, $R^1$, $R^2$, $R^3$, $R^4$, $R^5$, $R^6$ or $R^7$ can, as alkyl, be unbranched or branched alkyl. If this is $C_1$–$C_4$-alkyl, it can be, for example, methyl, ethyl, n-propyl, isopropyl, n-butyl, sec.butyl, isobutyl or tert.-butyl. R, $R^1$, $R^3$, $R^4$, $R^5$, $R^6$ and $R^7$ can also be $C_5$–$C_{12}$-alkyl, for example pentyl, hexyl, n-octyl, 2-ethylhexyl, 1,1,3,3-tetramethylbutyl, 1,1,3,3,5,5-hexamethylhexyl, n-decyl, isodecyl or n-dodecyl. $R^3$, $R^4$, $R^5$ and $R^7$ can also be $C_{13}$–$C_{20}$-alkyl, for example, tridecyl, tetradecyl, pentadecyl, hexadecyl, heptadecyl, octadecyl, nonadecyl or eicosyl.

As $C_3$–$C_{20}$-alkenyl, $R^3$, $R^4$ and $R^5$ can, for example, be allyl, methallyl, 2-butenhyl, 2-hexenyl, undecenyl, pentadecenyl, octadecenyl(oleyl) or decenyl.

As halogenoalkyl, R can, for example, be chloromethyl, trichloromethyl, bromomethyl, 2-chloroethyl, 2,2,2-trichloromethyl, trifluoromethyl or 2,3-dichloropropyl.

As alkoxy, alkylthio or alkylsulfonyl, R can, for example, be methoxy, ethoxy, isopropoxy, butoxy, hexyloxy, octyloxy, dodecyloxy, methylthio, tert.butylthio, dodecylthio, methylsulfonyl, ethylsulfonyl, hexylsulfonyl or dodecylsulfonyl. As alkylpehnyl, R can, for example, be tolyl, xylyl, 4-ethylphenyl, 4-tert.butylphenyl, 4-octylphenyl or 4-nonylphenyl.

As phenylalkyl, R, $R^3$ and $R^4$ can, for example, be benzyl, 1-phenylethyl, 2-phenylethyl, α,α-dimethylbenzyl or 2-phenylpropyl.

As cycloalkyl, R and $R^6$ can, for example, be cyclopentyl, cyclohexyl, cycloheptyl, methylcyclohexyl or cyclooctyl.

As phenyl which is substituted by halogen, $C_1$–$C_4$-alkyl, $C_1$–$C_4$-alkoxy or nitro, $R^1$ and $R^6$ can, for example, be 4-chlorophenyl, 3-bromophenyl, 2-fluorophenyl, p-tolyl, 3,5-dimethylphenyl, 4-isopropylphenyl, 4-methoxyphenyl, 3-ethoxyphenyl, 4-nitrophenyl or 4-nitro-2-methylphenyl.

As alkyl which is interrupted by O, $R^6$ and $R^7$ can, for example be 2-methoxyethyl, 2-butoxyethyl, 3,6-dioxaheltyl or 3,6-dioxadecyl. $R^7$ may also be polyethylene glycol residue having up to 20 C-atoms and up to 10 O-atoms.

When $R^3$ and $R^5$ together or $R^4$ and $R^5$ together form a ring fused to the phenolic moiety, the ring so formed is preferably a pyridine ring, a benzene ring or benzofuran ring, so producing a naphthol moiety, a hydroxyquinoline moiety or a hydroxydibenzofuran moiety.

Compositions containing a compound of the formula I in which one R is hydrogen, $C_1$–$C_4$-alkyl, $C_1$–$C_4$-alkoxy, trifluoromethyl, halogen or nitro and the other three R's are hydrogen, are preferred.

Compositions containing a compound of the formula I in which $R^1$ is hydrogen, $C_1$–$C_8$-alkyl, phenyl or furyl and $R_2$ is hydrogen, especially a compound of the formula I in which $R^1$ and $R^2$ are hydrogen, are also preferred.

Compositions containing a compound of the formula I in which $R^3$ and $R^4$ independently are hydrogen, $C_1$–$C_8$-alkyl, allyl, $C_7$–$C_{10}$-phenylalkyl, $C_1$–$C_4$-alkoxy, halogen, phenyl, cyclohexyl or a group —$CH_2CH_2COOR^7$, $R^5$ is hydrogen, $C_1$–$C_{18}$-alkyl, $C_3$–$C_{18}$-alkenyl or OH and $R^7$ is $C_1$–$C_{18}$-alkyl or $C_3$–$C_{20}$-alkyl which is interrupted by one or more oxygen atoms are also preferred.

In formula I, the phenolic OH group is preferably in the para-position or ortho-position relative to the group $>C(R^1)(R^2)$. If it is in the para position, preferred compounds are those of the formula III.

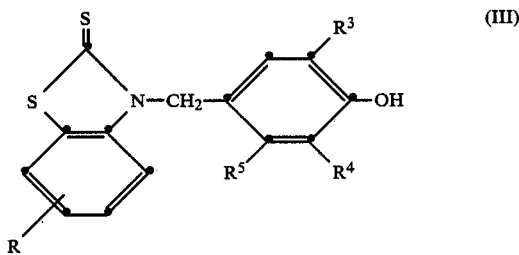

(III)

in which R is hydrogen, $C_1$–$C_4$-alkyl, $C_1$–$C_4$-alkoxy, chlorine, trifluoromethyl or nitro, $R^3$ and $R^4$ independently of one another are hydrogen, $C_1$–$C_8$-alkyl, allyl, chlorine, methoxy, $C_7$–$C_{10}$-phenylalkyl, phenyl or cyclohexyl and $R^5$ is H, $CH_3$ or OH.

If the phenolic OH group in formula I is in the ortho-position, preferred compounds are those of the formula IV

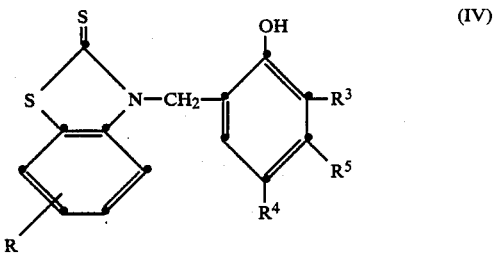

(IV)

in which R is hydrogen, $C_1$–$C_4$-alkyl, $C_1$–$C_4$-alkoxy, chlorine, trifluoromethyl or nitro, $R^3$ and $R^4$ independently are hydrogen, $C_1$–$C_8$-alkyl, $C_7$–$C_{10}$-phenylalkyl, phenyl, cyclohexyl or a group of the formula IIa

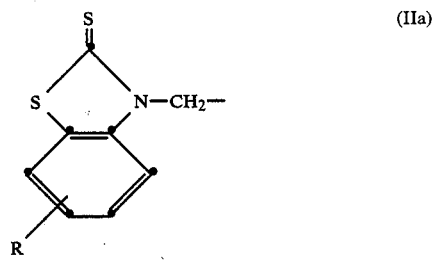

(IIa)

and $R^5$ is hydrogen, $C_1$–$C_{18}$-alkyl or $C_3$–$C_{18}$-alkenyl or $R^3$ and $R^5$ together form a benzene, pyridine or benzofuran ring fused to the phenolic ring.

Examples of individual compounds of the formula III are those containing the substituents indicated below:

| Compound No. | R | $R^3$ | $R^4$ | $R^5$ |
| --- | --- | --- | --- | --- |
| 1 | H | t-butyl | t-butyl | H |
| 2 | H | t-butyl | methyl | H |
| 3 | H | phenyl | phenyl | H |
| 4 | H | methyl | methyl | H |
| 5 | H | methyl | cyclohexyl | H |
| 6 | H | cyclohexyl | cyclohexyl | H |
| 7 | H | phenyl | t-butyl | H |
| 8 | H | methoxy | methoxy | H |
| 9 | H | chlorine | chlorine | H |
| 10 | H | isopropyl | isopropyl | H |
| 11 | H | 1-methylpropyl (sec.butyl) | 1-methylpropyl | H |
| 12 | H | methyl | ethyl | H |
| 13 | H | 1-phenylethyl | 1-phenylethyl | H |
| 14 | H | α,α-dimethylbenzyl | α,α-dimethylbenyzl | H |
| 15 | H | 1-methylheptyl (sec.octyl) | 1-methylheptyl | H |
| 16 | H | methyl | tert.butyl | methyl |
| 17 | H | methyl | tetramethylbutyl | methyl |
| 18 | 4-Cl | 1,1-dimethylpropyl (tert.amyl) | 1,1-dimethylpropyl | H |
| 19 | 5-$NO_2$ | 2-methylpropyl (isobutyl) | 2-methylpropyl | H |
| 20 | 5-$CF_3$ | t-butyl | t-butyl | H |
| 21 | H | methyl | methyl | methyl |
| 22 | 5-$NO_2$ | t-butyl | t-butyl | H |
| 23 | H | cyclohexyl | t-butyl | H |
| 24 | H | phenyl | methyl | H |

-continued

| Compound No. | R | $R^3$ | $R^4$ | $R^5$ |
|---|---|---|---|---|
| 25 | 5-Cl | t-butyl | t-butyl | H |
| 26 | 6-$C_2H_5O$ | t-butyl | t-butyl | H |
| 27 | H | H | H | H |
| 28 | H | methyl | allyl | H |
| 29 | H | isopropyl | isopropyl | OH |

Examples of individual compounds of the formula IV are those containing the following substituents:

| Compound No | R | $R^3$ | $R^4$ | $R^5$ |
|---|---|---|---|---|
| 30 | H | t-butyl | methyl | H |
| 31 | H | t-butyl | t-butyl | H |
| 32 | H | 1,1,3,3-tetramethyl-butyl | 1,1,3,3-tetramethyl-butyl | H |
| 33 | H | 1-methylpropyl | t-butyl | |
| 34 | H | 1,1-dimethyl-butyl (t-hexyl) | 1,1-dimethylbutyl | H |
| 35 | H | H | methyl | H |
| 36 | H | methyl | methyl | H |
| 37 | H | isopropyl | isopropyl | H |
| 38 | H | H | isopropyl | H |
| 39 | 5-Cl | t-hexyl | methyl | H |
| 40 | 5-$NO_2$ | H | H | H |
| 41 | 4-$CH_3$ | t-butyl | isopropyl | H |
| 42 | H | t-hexyl | isopropyl | H |
| 43 | H | H | α,α-dimethylbenzyl | H |
| 44 | 5-$NO_2$ | α,α-dimethylbenzyl | methyl | H |
| 45 | H | ethyl | α,α-dimethylbenzyl | H |
| 46 | H | t-butyl | α,α-dimethylbenzyl | H |
| 47 | H | α,α-dimethylbenzyl | α,α-dimethylbenzyl | H |
| 48 | H | 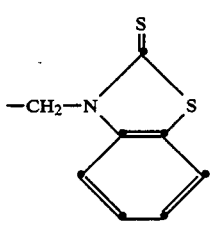 | methyl | H |
| 49 | H | methyl | 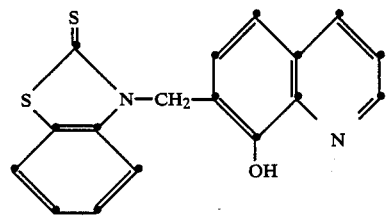 | H |
| 50 | H | t-amyl | t-amyl | H |
| 51 | H | sec.butyl | t-amyl | |
| 52 | H | H | H | t-butyl |
| 53 | H | H | H | pentadecyl |
| 54 | H | methyl | allyl | H |
| 55 | H | H | H | pentadecenyl |
| 56 | H | sec.butyl | sec.butyl | H |
| 57 | H | cyclohexyl | t-butyl | H |

58

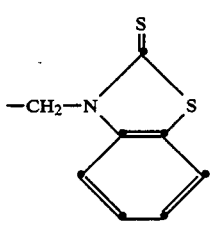

| Compound No | R | R³ | R⁴ | R⁵ |
|---|---|---|---|---|
| 59 | | | | |
| 60 | | | | |
| 61 | | | | |

Among the compounds of the formula I, the compound of the formula

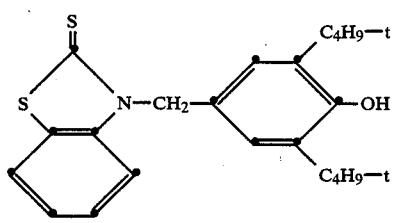

is a known compound. According to USSR Patent 1,164,233, this compound can be used as a metal deactivator in polyolefins.

All the other compounds of the formula I are novel compounds and, as such, also form a subject of the present invention.

The preparation of these compounds can be effected by heating the corresponding S-substituted isomers of the formula V

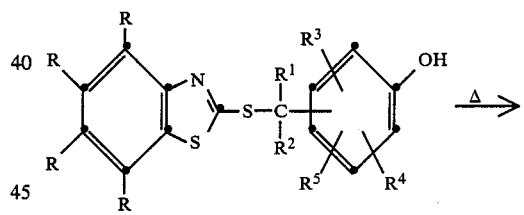

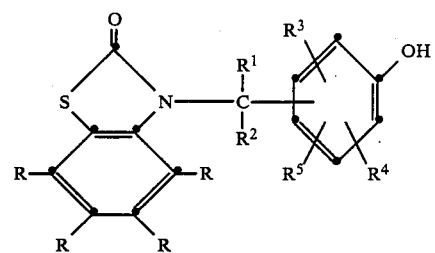

Heating can be carried out with or without a solvent. Examples of suitable solvents are aromatic hydrocarbons, such as toluene or xylene; halogenated hydrocarbons, such as tetrachloroethylene or chlorobenzene; alkanols, such as isopropanol or n-butanol; or esters, ketones, dimethylformamide or dimethyl sulfoxide. Polar solvents, for example dimethylformamide, accelerate the reaction. The rearrangement can also be accelerated by adding basic catalysts. Examples of the latter are, in particular, aliphatic, cycloaliphatic or heterocyclic amines. If the phenolic OH group is in the paraposition relative to the radical >C (R¹) (R²), the rearrangement proceeds more rapidly than if the group is in the ortho-position. The temperature required for the rearrangement therefore depends on the position of the OH group and on the solvent and catalyst used. It is preferably carried out at 70°–250° C., in particular at 100°–200° C.

The starting compounds of the formula V are known compounds or can be prepared analogously to the known compounds. Their preparation can be carried out by reacting the corresponding 2-mercaptobenzothiazoles VI with a carbonyl compound VII and a phenol VIII with acid catalysis in accordance with the equation.

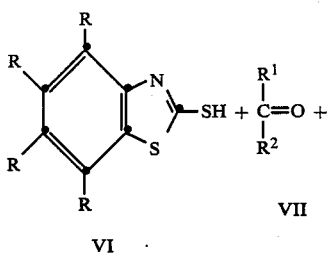

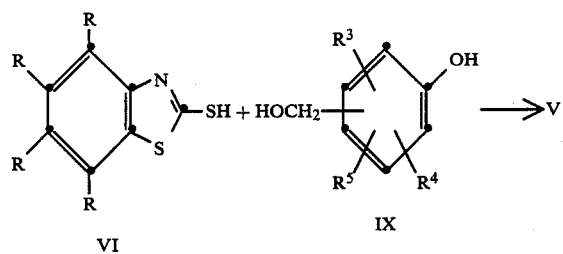

as described, for example, in U.S. Pat. No. 3,281,473. Alternatively, V can also be prepared from VI by reacting the latter with the corresponding benzyl alcohol IX:

as described, for example, in U.S. Pat. No. 3,215,641.

A second possible means of preparing compounds of he formula I is the reaction of 2-mercaptobenzothiazoles of the formula VI with an N-disubstituted aminomethylphenol of the formula X:

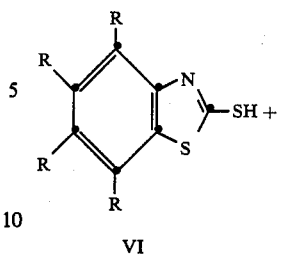

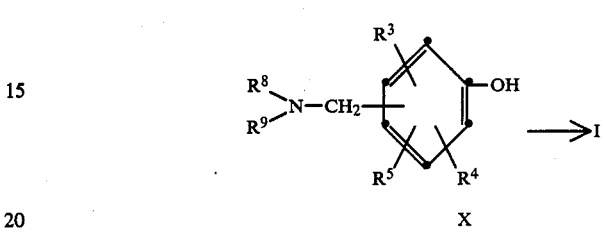

In these formulae, $R^8$ and $R^9$ independently of one another are $C_1$–$C_{12}$-alkyl, $C_5$–$C_8$-cycloalkyl, benzyl or phenyl. This reaction is described in USSR Patent 1,164,233. It is preferably carried out in a polar organic solvent. Examples of these are lower alkanols ($C_1$–$C_4$), dimethylformamide or dimethylsulfoxide. The reaction is carried out by heating at 50°–200° C., preferably 70°–150° C.

A third possible method of preparation is the reaction of a 2-mercaptobenzothiazole of the formula VI with a carbonyl compound of the formula VII and a phenol of the formula VIII with base catalysis:

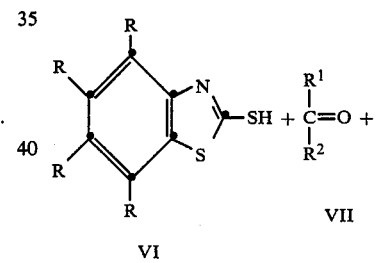

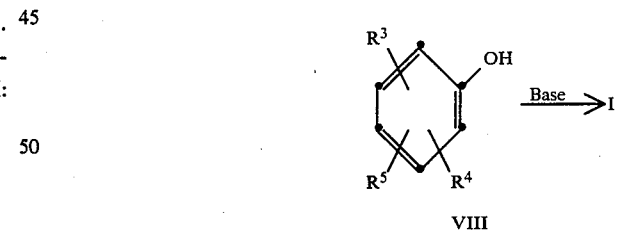

Whereas, as previously described, the S-substituted isomers of the formula V are formed with acid catalysis, the N-substituted isomers of the formula I are formed in the same reaction with base catalysis.

The reaction is preferably carried out in a polar solvent by heating at 50°–150° C., preferably 70°–120° C.

Suitable base catalysts are any known organic or inorganic strong bases. It is preferable to use primary, secondary or tertiary amines, for example isopropylamine, butylamine, cyclohexylamine, dibutylamine, dihexylamine, di(isopropyl)-amine, triethylamine, tributylamine, piperidine, morpholine, pyrrolidine or quinoline. The reaction is particularly suitable if formaldehyde is used as the carbonyl compound, with the formation of products of the formula I in which $R^1=R^2=H$. The formaldehyde can be used, for example as an aqueous solution (formalin) or in the form of paraformaldehyde, or a reagent which forms formaldehyde under the reaction conditions, for example hexamethylenetetramine, is used.

This reaction is also suitable for the preparation of compounds of the formula I in which $R^3$ or $R^4$ is a group of formula II. In this case use is made of a phenol of formula VIII in which $R^3$ or $R^4$ is hydrogen and it is reacted with at least two equivalents of mercaptobenzothiazole of the formula VI and at least two equivalents of the carbonyl compound of the formula VII:

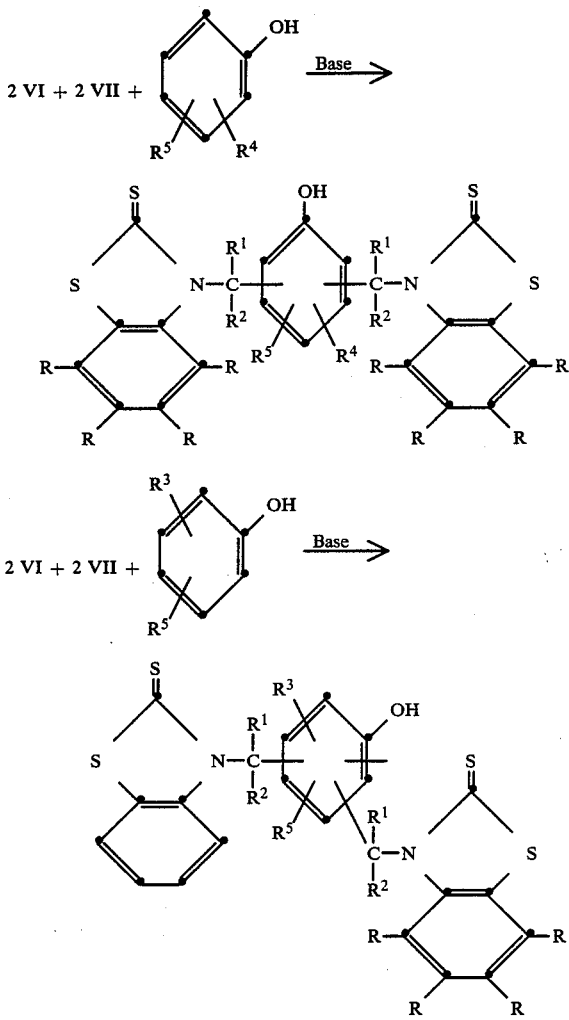

The compounds of the formula I are effective as corrosion inhibitors and as antioxidants. As such, they can be added to any liquid or solid organic materials. They are preferably used in coating materials or lubricants.

Examples of coating materials ae lacquers, paints or varnishes. They always contain a film-foring binder as well as other optional components.

Examples of coating materials are materials based on an epoxide, polyurethane, aminoplast, acrylic, alkyld or polyester resin and on mixtures of such resins. Further examples of suitable binders are vinyl resins, such as polyvinyl acetate, polyvinylbutyral, polyvinyl chloride and copolymers thereof, cellulose esters, chlorinated rubbers, phenolic resins, styrene/butadiene copolymers and drying oils.

The coating materials can contain solvents or can be free from solvents or they can be aqueous systems (dispersions, emulsions or solutions). They can be pigmented or non-pigmented and they can also be metallized. In addition to the corrosion inhibitors according to the invention, they can contain other additives customary in the technology of coating materials, for example fillers, flow control auxiliaries, dispersing auxiliaries, thixotropic agents, adhesion promoters, antioxidants, light stabilizers or curing catalysts. They can also contain other known anticorrosion agents, for example anti-corrosion pigments, such as pigments containing phosphates or borates, or metal oxide pigments, or other organic or inorganic corrosion inhibitors, for example salts of nitroisophthalic acid, phosphorus esters, technical amines or substituted benzotriazoles.

It is also advantageous to add basic fillers or pigments which, in certain binder systems, produce a synergistic effect on the inhibition of corrosion. Examples of such basic fillers and pigments are calcium carbonate, magnesium carbonate, zinc oxide, zinc carbonate, zinc phosphate, magnesiumm oxide, aluminium oxide, aluminium phosphate or mixtures thereof. Examples of basic organic pigments are pigments based on aminoanthraquinone.

The corrosion inhibitor can also be applied to a carrier. Pulverulent fillers of pigments are particularly suitable for this purpose. This technique is described in greater detail in DE-A 3,122,907.

The corrosion inhibitors can be added to the coating material during its preparation, for example during the distribution of pigments by grinding, or the inhibitor is dissolved in a solvent beforehand and the solution is stirred into the coating agent. The inhibitor is used in an amount of 0.1 to 20% by weight, preferably 0.5 to 5% by weight, based on the solids content of the coating material.

The coating materials can be applied to the substrate by any customary process, for example by spraying, dipping, brushing or by electrodeposition, in particular cathodic deposition. Several layers are often applied. The corrosion inhibitors are added primarily to the base layer, since they act particularly on the metal/coating interface. It is also possible, however, additionally to add the inhibitors to the top layer of intermediate layer, where they are available as a depot. Depending on whether the binder is a physically drying resin or a heat-curable or radiation-curable resin, the coating is cured at room temperature or by heating (stoving) or by irradiation.

The coating material preferably is a primer for metallic substrates, such as iron, steel, copper, zinc or aluminium. If the coating material is an aqueous system it may be applied to the metallic substrate preferably by cathodic electrodeposition.

In addition to the anticorrosive effect the compounds of formula I have a favourable effect on the adhesion of coating to metal. They further exert an antioxidative and light-stabilizing action on the coating and thus reduce the chalking of pigments and fillers on outdoor exposure. All these properties contribute towards prolonging the useful life of the coating.

Examples of lubricants to which the corrosion inhibitors according to the invention can be added are lubricating oils and lubricating greases. The lubricating oils can be mineral oils or synthetic oils or mixtures of both. Examples of synthetic oils are those based on phosphoric acid esters, polyalkylene oxides, α-olefin polymers, triesters of trimethylolpropane or tetraesters of pentaerythritol or aliphatic polyesters.

The lubricants can contain further additives, for example anti-oxidants, pour-point depressants, viscosity index improvers, metal deactivators, dispersing agents, high-pressure additives or anti-wear additives. They can also contain other corrosion inhibitors, for example organic acids and esters, metal salts, amine salts or anhydrides thereof, heterocyclic compounds, phosphoric acid partial esters and amine salts thereof or metal salts of sulfonic acids.

It is of considerable importance for the use of the compounds of the formula I in lubricants that these compounds also act as antioxidants, since multi-purpose additives are particularly valuable in this field.

The compounds of the formula I are used in lubricants in an amount of 0.01 to 5% by weight, in particular 0.2 to 2% by weight.

Both for coating materials and for lubricants it can be important to add a mixture of several compounds of the formula I. For example, if certain technical mixtures of phenols are used in the preparation of the compounds of the formula I, a mixture of products of the formula I is inevitably formed, and this can be used as such. However, in order to lower the melting point it can also be advantageous to mix two or more of such compounds.

The preparation and use of compounds of the formula I are described in greater detail in the following examples. In these parts and percentages are by weight, unless stated otherwise. The temperature is quoted in °C.

EXAMPLE 1

2.0 g of 2-(3,5-di-tert.-butyl-4-hydroxybenzylthio)-benzothiazole (prepared as specified in U.S. Pat. No. 3,215,641, Example 1) are dissolved in 10 ml of dimethylformamide (DMF), and the solution is heated at 150° for 2.5 hours under $N_2$. The solvent is then distilled off in vacuo and the yellowish crude product is recrystallized from ethanol. This gives 1.8 g of 3-(3,5-ditert.-butyl-4-hydroxybenzyl)-benzothiazole-2-thione of melting point 148°–150° (compound No. 1).

EXAMPLE 2

The procedure described in Example 1 is repeated using 2-(3-tert.butyl-2-hydroxy-5-methylbenzylthio)-benzothiazole, and 3-(3-tert.butyl-2-hydroxy-5-methylbenzyl)-benzothiazole-2-thione, melting at 178°–180°, (compound No. 30) is obtained.

EXAMPLE 3

135.2 g of a 40% aqueous solution of dimethylamine (1.2 mol) are added, with rapid stirring to a suspension of 264.3 g (1 mol) of 2,6-diphenylphenol in 1.5 l of 95% ethanol and 20 g of DMF. 98.3 g of a 37% aqueous solution of formaldehyde are then added dropwise in the course of 30 minutes at room temperature. The suspension is stirred for 70 hours at room temperature and is then filtered. The filter residue is washed with cold 80% ethanol and is recrystallized from 1.5 l of acetonitrile. This gives 262.9 g of N,N-dimethyl-3,5-diphenyl-4-diphenyl-4-hydroxybenzylamine, melting at 136°–137°.

30.3 g of (0.1 mol) of this amine and 16.7 g (0.1 mol) of mercaptobenzothiazole are dissolved in 100 ml of DMF, and the solution is heated at 110° for 42 hours under $N_2$. The solution is then evaporated in vacuo and the residual oil is crystallized from ethanol. This gives 42.6 g of 3-(3,5-diphenyl-4-hydroxybenzyl)-benzothiazole-2-thione in the form of yellow crystals, melting at 145°–146° (compound No. 3).

EXAMPLE 4

3-(3,5-ditert.-butyl-4-hydroxybenzyl)-benzothiazole-2-thione, melting at 152°–154° after being recrystallized twice, (compound No. 1) is obtained analogously to Example 3 from N,N-di-methyl-3,5-ditert.-butyl-4-hydroxybenzylamine.

EXAMPLE 5

3-(3-tert.-butyl-4-hydroxy-5-methylbenzyl)-benzothiazole-2-thione of melting point 153°–155° (compound No. 2) is obtained analogously to Example 3 from N,N-dimethyl-3-tert.-butyl-4-hydroxy-5-methylbenzylamine and 2-mcercaptobenzothiazole.

EXAMPLE 6

66.9 g (0.4 mol) of 2-mercaptobenzothiazole and 82.5 g (0.4 mol) of 2,6-ditert.-butylphenol are suspended in 100 ml of DMF. 43 g of 35% aqueous formaldehyde solution (0.5 mol) and 2.6 g (0.02 mol) of dibutylamine are added, and the dispersion is stirred at 90° for 4 hours under $N_2$. The reaction mixture is evaporated in vacuo and the resulting crude product is recrystallized from ethyl acetate/hexane. This gives 120 g of 3-(3,5-ditert.-butyl-4-hydroxybenzyl)-benzothiazole-2-thione in the form of a yellow powder melting at 148°–151° (compound No. 1).

EXAMPLE 7

3-(3-tert.-butyl-4-hydroxy-5-methylbenzyl)-benzothiazole-2-thione, melting at 156°–157° after being recrystallized twice form 70% aqueous ethanol, (compound No. 2) is obtained analogously from 2-tert.-butyl-6-methylphenol, 2-mercaptobenzothiazole and formaldehyde using dibutylamine as catalyst.

EXAMPLE 8

3-(3,5-diisopropyl-4-hydroxybenzyl)-benzothiazole-2-thione, melting at 114°–115° after recrystallization from ethyl acetate/petroleum ether, (compound No. 10) is obtained analogously from 0.2 mol of 2,6-diisopropylphenyl, 0.2 mol of 2-mercaptobenzothiazole and 0.25 mol of formaldehyde in 175 ml of DMF.

EXAMPLE 9

3-(3,5-dimethyl-4-hydroxybenzyl)-benzothiazole-2-thione of melting point 164°–165° (compound No. 4) is obtained analogously to Example 8, using 2,6-dimethylphenol.

EXAMPLE 10

By analogous method to example 6 the following compounds are synthesized:
3-(3,5-di-sec.butyl-4-hydroxybenzyl)-benzothiazole-2-thione (compound No. 11), syrup;
3-(3,5-di-cyclohexyl-4-hydroxybenzyl)-benzothiazole-2-thione (compound No. 6), m.p. 184°;
3(3-cyclohexyl-5-tert.butyl-4-hydroxybenzyl)-benzothiazole-2-thione (compound No. 23), m.p. 149°;
3-(3-phenyl-5-methyl-4-hydroxybenzyl)-benzothiazole-2-thione (compound No. 24), m.p. 147°–149°;
3(3-methyl-5-cyclohexyl-4-hydroxybenzyl)-benzothiazole-2-thione (compound No. 5), m.p. 148°;

3-(2,3,5-trimethyl-4-hydroybenzyl)-benzothiazole-2-thione (compound No. 21), m.p. 227°-228°;
5-chloro-3-(3,5-di-tert.butyl-4-hydroxybenzyl)-benzothiazole-2-thione (compound No. 25), m.p. 147°-149°;
6-ethoxy-3-(3,5-di-tert.butyl-4-hydroxybenzyl)-benzothiazole-2-thione (compound No. 26), m.p. 184°;
5-nitro-3-(3,5-di-tert.butyl-4-hydroxybenzyl)-benzothiazole-2-thione (compound No. 22);
5-trifluoromethyl-3-(3,5-di-tert-butyl-4-hydroxybenzyl)-benzothiazole-2-thione (compound No. 20), m.p. 161°-162°;
3-(3-methyl-5-allyl-4-hydroxybenzyl)-benzothiazole-2-thione (compound No. 28), m.p. 104°-106°.

EXAMPLE 11

3-(3,5-di-tert.butyl-2-hydroxybenzyl)-benzothiazole-2-thione (compound 31) is prepared by heating 0.2 mol 2-mercaptobenzothiazole, 0.2 mol of 2,4-di-tert.butylphenol and 0.2 mol of paraformaldehyd in the presence of 1 ml of dibutylamine at 150° for 4 hours and crystallising the product from ethanol.

$C_{22}H_{27}N_4S_2O$; calc. C=68.75%, H=7.11%, N=3.66%. found C=68.57%, H=7.01%, N=3.63%.

By analogous procedure the following compounds can be made.

3-(3,5-dimethyl-2-hydroxybenzyl)-benzothiazole-2-thione (compound No. 36), m.p. 155°-157°;
3-(3,5-di-isopropyl-2-hydroxybenzyl)-benzothiazole-2-thione (compound No. 37), m.p. 150°-152°;
3-(3,5-di-tert.amyl-2-hydroxybenzyl)-benzothiazole-2-thione (compound No. 50), m.p. 155°-158°;
3-(3-sec.butyl-5-tert.amyl-2-hydroxybenzyl)-benzothiazole-2-thione (compound No. 51), m.p. 104°-107°;
3-(3,5-di-tert.octyl-2-hydroxybenzyl)-benzothiazole-2-thione (compound No. 32), m.p. 122°;
3-(4-tert.butyl-2-hydroxybenzyl)-benzothiazole-2-thione (compound No. 52), m.p. 121°-126°;
3-(4-pentadecyl-2-hydroxybenzyl)-benzothiazole-2-thione (compound No. 53), m.p. 105°-106°;
3-(4-pentadecenyl-2-hydroxybenzyl)-benzothiazole-2-thione (compound No. 55), red syrup;
3-(3-methyl-5-allyl-2-hydroxybenzyl-benzothiazole-2-thione (compound No. 54), m.p. 90°-93°.

EXAMPLE 12

16.7 g of mercaptobenzothiazole, 3.0 g of paraformaldehyde, 15.4 g of 2,6-dimethoxyphenol and 1 g dibutylamine are heated at 110°, with rapid stirring, for 2 hours. 50 ml of ethanol are added and the mixture cooled to 10° thereby obtaining 27.3 g of 3-(3,5-dimethoxy-4-hydroxybenzyl)-benzothiazole-2-thione (compound No. 8) melting at 141°-142°.

Analysis: $C_{16}H_{15}NO_3S_2$ Calc. S=19.13%, found S=19.22%

Using the same procedure but replacing the dimethoxy phenol by 16.3 g of 2,6-dichlorophenol yields 24.3 g of 3-(3,5-dichloro-4-hydroxybenzyl)-benzothiazole-2-thione (compound No. 9), m.p. 169°-172°.

Analysis: $C_{14}H_9NOS_2Cl_2$ calc. Cl=20.96%, found Cl=20.76%.

EXAMPLE 13

Using the procedure of example 12 33.4 g of mercaptobenzothiazole, 6 g of paraformaldehyde, 31.8 g of 8-hydroxyquinaldine and 2 ml of dibutylamine are reacted to give 64 g of 3-(2-methyl-8-hydroxyquinolin-7-ylmethyl)-benzothiazole-2-thione (compound No. 60) melting at 211°-215°.

Using the same procedure but replacing the hydroxyquinaldine by 36.8 g of 2-hydroxydibenzofuran yields 41 g of 3-(2-hydroxy-dibenzofuran-1-ylmethyl)-benzothiazole-2-thione (compound No. 61) melting at 174°-180°.

EXAMPLE 14

6.8 g of 2-(5-nitro-2-hydroxybenzylthio)-benzothiazole in 30 ml of dimethylformamide containing 0.2 g of dibutylamine are heated under reflux for 12 hours. Evaporation of the solvent and column chromatography gives 3 g of 3-(5-nitro-2-hydroxybenzyl)-benzothiazole-2-thione (compound No. 40) melting at 231°.

EXAMPLE 15

An alkyd resin paint is prepared in accordance with the following formulation:
40 parts of Alphthalate ®380 (60% solution in xylene), alkyd resin made by Reichhold Albert Chemie AG,
10 parts of iron oxide red 225 made by Bayer Ag,
13.6 parts of talc (micronized),
13 parts of micronized calcium carbonate (Millicarb ®, Pluss-Staufer AG)
0.3 part of skin prevention agent Luaktin ®(BASF),
0.6 part of 8% solution of cobalt naphthenate and
22.5 parts of 6:40 xylene/ethylglycol mixture.

The paint is ground with glass beads to a pigment and filler particle size of 10–15 μm. The corrosion inhibitors indicated in the table below are added before grinding.

The paint is sprayed onto sand-blasted steel sheets measuring 7×13 cm in a layer thickness amounting to approx. 50 μm after drying. After drying at room temperature for 7 days, the samples are subjected to after-curing at 60° for 60 minutes.

Two cruciform cuts of length 4 cm are cut, down to the metal, in the cured paint surface by means of a Bonder Cross-cut apparatus. The edges are protected by applying en edge-protection agent (Icosit ®255) to the latter.

The samples are now subjected to a salt spray test as specified in ASTM B 117 of a duration of 600 hours. After every 200 hours weathering, the state of the coating is assessed, specifically the degree of bubbling (as specified in DIN 53,209) at the cross-cut and on the painted surface and also the degree of rusting (as specified in DIN 53,210) on the whole surface.

At the end of the tests, the coating is removed by treatment with concentrated sodium hydroxide solution, and the corrosion of the metal at the cross-cut (as specified in DIN 53,167) and over the remainder of the surface is assessed. In each case the assessment is carried out in accordance with a 6-point scale. The sum of the assessment of the coating and the assessment of the metal surface gives the anti-corrosion value AC. The higher this is the more effective is the inhibitor tested.

TABLE 1

| Corrosion inhibitor | Results of the salt spray test | | | |
|---|---|---|---|---|
| | Amount added* | Assessment of coating | Assessment of metal | AC |
| None | — | 2.2 | 1.7 | 3.9 |
| Compound No. 1 | 2% | 5.0 | 5.1 | 10.1 |
| Compound No. 2 | 2% | 3.9 | 4.2 | 8.1 |
| Compound No. 3 | 4% | 4.4 | 4.6 | 9.0 |
| | 2% | 4.9 | 3.9 | 8.8 |
| | 4% | 5.1 | 4.7 | 9.8 |
| Compound No. 4 | 4% | 2.9 | 2.0 | 4.9 |
| Compound No. 6 | 4% | 3.5 | 2.4 | 5.9 |
| Compound No. 11 | 4% | 3.3 | 2.3 | 5.6 |
| Compound No. 20 | 2% | 4.4 | 4.5 | 8.9 |

TABLE 1-continued

| Corrosion inhibitor | Results of the salt spray test | | | |
|---|---|---|---|---|
| | Amount added* | Assessment of coating | Assessment of metal | AC |
| Compound No. 21 | 2% | 4.8 | 5.2 | 10.0 |
| Compound No. 22 | 2% | 4.0 | 5.2 | 9.2 |
| Compound No. 23 | 2% | 4.4 | 4.5 | 8.9 |
| Compound No. 25 | 2% | 4.8 | 2.3 | 7.1 |
| Compound No. 26 | 2% | 2.9 | 3.3 | 6.2 |
| Compound No. 27 | 2% | 3.8 | 5.1 | 8.9 |
| Compound No. 29 | 2% | 3.7 | 3.0 | 6.7 |
| Compound No. 32 | 4% | 3.9 | 2.0 | 5.9 |
| Compound No. 38 | 2% | 4.3 | 4.5 | 8.8 |
| Compound No. 43 | 2% | 3.6 | 5.0 | 9.6 |
| Compound No. 49 | 2% | 4.4 | 4.5 | 8.9 |
| Compound No. 50 | 4% | 3.0 | 1.9 | 4.9 |
| Compound No. 51 | 2% | 3.9 | 3.1 | 7.0 |
| Compound No. 52 | 2% | 4.5 | 4.5 | 9.0 |
| Compound No. 53 | 2% | 5.8 | 5.8 | 11.6 |
| Compound No. 55 | 2% | 4.0 | 4.9 | 8.9 |
| Compound No. 56 | 4% | 3.3 | 2.3 | 5.6 |
| Compound No. 58 | 4% | 2.0 | 3.2 | 5.2 |
| Compound No. 59 | 4% | 3.7 | 3.1 | 6.8 |

*Based on the solids content of the paint.

EXAMPLE 16

Steel panels coated with an alkyd resin paint are prepared according to the procedure of example 15. The samples were exposed to natural weathering in North Carolina near the sea shore for 15 months. Afterwards the breadth of the rust zone along the cut is measured according to ASTM D 1654–79a. The results are given in Table 2.

TABLE 2

| Corrosion inhibitor | Breadth of rust zone mm |
|---|---|
| none | 2–3 |
| 2% Compound No. 1 | 0.5–1 |
| 2% Compound No. 2 | 0.5–1 |
| 2% Compound No. 3 | 0–0.5 |

EXAMPLE 17

A black pigmented cathodic primer prepared according to U.S. Pat. No. 4,148,772 (Example I) is electrodeposited on zincphosphated steel panels in a thickness of 20 μm and stoved for 20 minutes at 180°. The samples are subjected to the salt spray test (ASTM B 117) for 600 hours and the corrosion is assessed as described in example 15. The results are shown in Table 3.

TABLE 3

| Corrosion Inhibitor | Assessment of Coating | Metal | AC |
|---|---|---|---|
| none | 2.2 | 1.3 | 3.5 |
| 2% Compound No. 1 | 3.4 | 5.0 | 8.4 |

EXAMPLE 18

A primer is prepared from the following components:

| | |
|---|---|
| Aromatic epoxy resin Beckopox ® EP 301 (50% solution) | 16 parts |
| Polyvinylbutyral resin Mowital ® B 30 HH (20% solution) | 40 parts |
| Talc (micronized) | 8 parts |
| Iron oxide red 225 (Bayer AG) | 12 parts |
| Barium sulfate | 2 parts |
| Curing agent Beckopox ® EH 614 | 2 parts |
| Xylene | 10 parts |
| Butanol | 5 parts |
| Propylene glycol monobutylester | 5 parts |

The primer is sprayed onto degreased steel panels in a thickness of 40 μm. After 7 days air drying the samples are subjected to the salt spray test (ASTM B 117) for 600 h. The assessment of the corrosion is carried out as described in example 15. The results are shown in Table 4.

TABLE 4

| Corrosion Inhibitor | Assessment of Coating | Metal | AC |
|---|---|---|---|
| none | 2.2 | 3.1 | 5.3 |
| 2% Compound No. 1 | 2.5 | 4.6 | 7.1 |

EXAMPLE 19

Samples coated with a cathodic deposited black primer are prepared as described in example 17. The hardened samples are weathered in a Xenon-Weatherometer for 200 hours. The 60°-gloss was measured by a reflexion-photometer. Without addition of a stabilizer there was a rapid decrease of the gloss caused by photodegradation of the binder system and chalking out of the pigment, as is shown in Table 5.

TABLE 5

| Stabilizer | % Gloss retention after 100 h | after 200 h exposure |
|---|---|---|
| none | 62 | 5 |
| 2% Compound No. 1 | 86 | 55 |

The same samples were exposed to natural weathering in Florida (45° south) for one month. The results are shown in Table 6.

TABLE 6

| Stabilizer | % Gloss retention after 1 month Florida exposure |
|---|---|
| none | 32 |
| 2% Compound No. 1 | 74 |

EXAMPLE 20

A gray-pigmented commercial cathodic deposible primer is deposited onto steel panels in a thickness of 20 μm and is stoved at 170° for 30 minutes. A clear coating is sprayed onto the primer consisting of a two-component polyurethane resin in a thickness of 40 μm. After stoving for 30 minutes at 120° the samples are exposed to a Xenon-Weatherometer for 1200 hours. The yellowing caused by weathering was assessed by measuring the colour shade distance from the original shade ΔE using a Macbeth Colorimeter. The stabilizer was added to the primer. The results are shown in Table 7.

TABLE 7

| Stabilizer | ΔE after 400 h | 800 h | 1200 h WOM |
|---|---|---|---|
| none | 6.8 | 8.0 | 8.9 |
| 2% Compound No. 1 | 2.4 | 3.6 | 4.7 |

EXAMPLE 21

The cathodic primer of example 17 was electrodeposited on zincphosphated steel panels in a thickness of 30

μm and was stoved for 20 minutes at 180°. A white top coating was applied onto the primer consisting of a two-component polyurethane resin pigmented with titan dioxide. The thickness of the top coat was 30 μm. A stabilizer was added to a part of the primer in an amount of 2% based on the primer resin.

The samples were stoved at 150° in an air-circulated oven. The yellowness index of the samples was measured after certain time intervals using a barium sulfate standard. The results are shown in Table 8.

TABLE 8

| Stabilizer | Yellowness index after | | |
|---|---|---|---|
| | 5 h | 9 h | 24 h |
| none | 2.2 | 3.4 | 8.2 |
| 2% Compound No. 1 | 1.1 | 2.0 | 5.2 |

The results show that the corrosion inhibitor exerts a marked antioxidative activity.

EXAMPLE 22

This example shows the antioxidative effect in lubricating oils. The used test is a modified version of the "Rotary Bomb Oxidation Test for Mineral Oils" (ASTM D 2272). It is described in detail by C. S. Ku and S. M. Hsu in Lubrication Engineering, Vol. 40(2), 75-83 (1984). The test oil used is an engine oil based on mineral oil, which contains half the conventional amount of zinc dithiophosphate (0.75%; zinc content 0.06%, based on the engine oil).

The stabiliser under test is tested in the described engine oil in the presence of 2% water, a liquid, oxidised, nitrated fraction of a petroleum, as catalyst, (4% charge concentration) and a liquid metal naphthenate, as further catalyst, (4% charge concentration). Water, and the two liquid catalyst compounds are supplied under the No. Standard Reference Material 1817 by the National Bureau of Standards (NBS) with analysis certificate. The experiment is completed at a significant break in the pressure/time diagram. The results given in the Table denote the time (in minutes) up to the break in the pressure/time diagram.

Long times correspond to good stabiliser activity. Concentration of the stabiliser: 0.5 wt %, based on the oil.

TABLE 9

| Stabiliser | Minutes until significant pressure drop |
|---|---|
| none | 86 |
| Compound No. 31 | 134 |

What is claimed is:

1. A composition composed of a coating material and containing 0.1 to 20% by weight, based on the solids content of the coating material, of at least one compound of the formula I

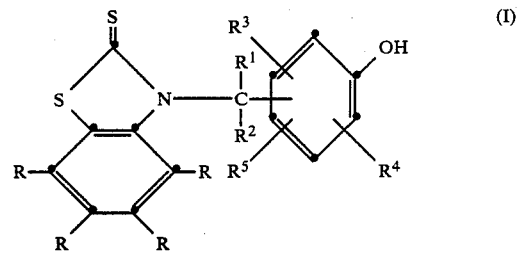

in which each R independently of one another is hydrogen, $C_1$–$C_{12}$-alkyl, $C_1$–$C_4$-halogenalkyl, $C_1$–$C_{12}$-alkoxy, $C_1$–$C_{12}$-alkylthio, phenylthio, benzylthio, $C_1$–$C_{12}$-alkylsulfonyl, phenyl, $C_7$–$C_{15}$-alkylphenyl, $C_7$–$C_{10}$-phenylalkyl, $C_5$–$C_8$-cycloalkyl, halogen, —$NO_2$, —CN, —COOH, —COO—($C_1$–$C_4$-alkyl), —OH, —$NH_2$, —$NHR^6$, —$N(R^6)_2$, —$CONH_2$, —$CONHR^6$ or —$CON(R^6)_2$, $R^1$ is hydrogen, $C_1$–$C_{12}$-alkyl, phenyl, phenyl which is substituted by halogen, $C_1$–$C_4$-alkyl, $C_1$–$C_4$-alkoxy or —$NO_2$, pyridyl, thienyl, or furyl, $R^2$ is hydrogen or $C_1$–$C_4$-alkyl, $R^3$ and $R^4$ independently of one another are hydrogen, halogen, $C_1$–$C_4$-alkoxy, cyano, nitro, $C_1$–$C_{20}$-alkyl, —$(CH_2)_m$—$COOR^7$, —$(CH_2)_m$—$CONHR^6$, —$(CH_2)_m$—$CON(R^6)_2$, $C_3$–$C_{20}$-alkenyl, $C_7$–$C_{10}$-phenylalkyl, phenyl, cyclohexyl, cyclopentyl or a group of the formula II

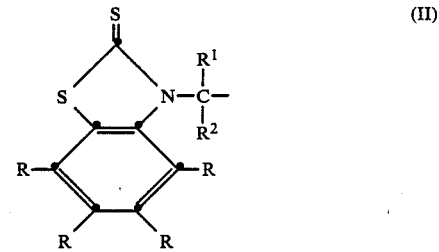

$R^5$ is hydrogen, $C_1$–$C_{20}$-alkyl, $C_3$–$C_{20}$-alkenyl or hydroxy, or $R^3$ and $R_5$ together or $R^4$ and $R^5$ together form a ring fused to the phenolic moiety which ring may be a carbocyclic or heterocyclic ring containing oxygen, nitrogen or sulfur as heteroatoms, each ring being optionally substituted by $C_1$–$C_4$-alkyl, $C_1$–$C_4$-alkoxy or halogen, $R^6$ is $C_1$–$C_{12}$-alkyl, $C_3$–$C_{12}$-alkyl which is interrupted by one or more O atoms, $C_5$–$C_8$-cycloalkyl, benzyl, phenyl, or phenyl which is substituted by halogen, $C_1$–$C_4$-alkyl, $C_1$–$C_4$-alkoxy or nitro, or —$N(R^6)_2$ is a pyrrolidino, piperidino or morpholino group, $R^7$ is hydrogen or $C_1$–$C_{20}$-alkyl, which may be substituted by halogen or hydroxyl or $R^7$ is $C_3$–$C_{20}$-alkyl which is interrupted by one or more oxygen atoms and may be substituted by hydroxyl and m is 0, 1 or 2.

2. A composition according to claim 1, wherein, in formula I and II, one R is hydrogen, $C_1$–$C_4$-alkyl, $C_1$–$C_4$-alkoxy, halogen, trifluoromethyl or nitro and the other three R's are hydrogen.

3. A composition according to claim 1, wherein in formula I, $R^1$ is hydrogen, $C_1$–$C_8$-alkyl, phenyl or furyl and $R^2$ is hydrogen.

4. A composition according to claim 1, wherein $R^1$ and $R^2$ in formula I are hydrogen.

5. A composition according to claim 1, wherein, in formula I, $R^3$ and $R^4$ independently of one another are hydrogen, $C_1$-$C_8$-alkyl, allyl, $C_7$-$C_{10}$-phenylalkyl, $C_1$-$C_4$-alkoxy, halogen, phenyl, cyclohexyl, or a group —$CH_2CH_2COOR^7$, $R^5$ is hydrogen, $C_1$-$C_{18}$-alkyl, $C_3$-$C_{18}$-alkenyl or OH and $R^7$ is $C_1$-$C_{18}$-alkyl or $C_3$-$C_{20}$-alkyl which is interrupted by one or more oxygen atoms.

6. A composition according to claim 1, containing a compound of the formula III

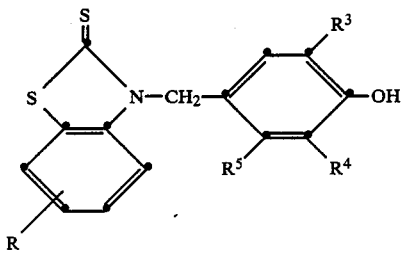

wherein R is hydrogen, $C_1$-$C_4$-alkyl, $C_1$-$C_4$-alkoxy, chlorine, trifluoromethyl or nitro, $R^3$ and $R^4$ independently of another are hydrogen, $C_1$-$C_8$-alkyl, allyl, chlorine, methoxy, $C_7$-$C_{10}$-phenylalkyl, phenyl or cyclohexyl and $R^5$ is hydrogen, methyl or OH.

7. A composition according to claim 1, containing a compound of the formula IV

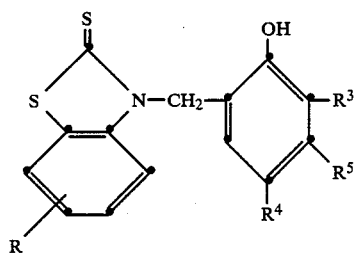

in which R is hydrogen, $C_1$-$C_4$-alkyl, $C_1$-$C_4$-alkoxy, chlorine, trifluoromethyl or nitro, $R^3$ and $R^4$ independently are hydrogen, $C_1$-$C_8$-alkyl, $C_7$-$C_{10}$-phenylalkyl, phenyl cyclohexyl or a group of the formula IIa

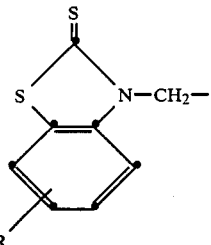

and $R^5$ is hydrogen, $C_1$-$C_{18}$-alkyl, $C_3$-$C_{18}$-alkenyl or $R^3$ and $R^5$ together form a benzene, pyridine or benzofuran ring fused to the phenolic ring.

8. A composition according to claim 1 which is a primer for metallic substrates.

9. A composition according to claim 8 which is a primer on iron, steel, copper, zinc or aluminium.

10. A composition according to claim 1 which is an aqueous coating material.

11. A composition according to claim 10 which is a cathodic deposible coating material.

12. A coating material composition according to claim 1 containing 0.5 to 5 percent by weight, based on the solids content of the composition, of at least one compound of formula I as defined in claim 1.

13. A composition according to claim 1 containing a coating material selected from the group consisting of an epoxide, polyurethane, aminoplast, acrylic, alkyd or polyester resin a mixture of such resins.

14. A composition according to claim 1 containing a coating material on the basis of a vinyl resin, cellulose ester, chlorinated rubber, phenolic resin, styrene-butadiene copolymer and a drying oil.

15. A composition according to claim 1 containing the compound 3-(3,5-di-tert.butyl-4-hydroxybenzyl)-benzothiazole-2-thione.

16. A composition according to claim 1 containing the compound 3-(4-pentadecyl-2-hydroxybenzyl)-benzothiazole-2-thione.

17. A composition according to claim 1 containing the compound 3-(4-hydroxybenzyl)-benzothiazole-2-thione.

18. A composition according to claim 1 containing the compound 3-(2,3,5-trimethyl-4-hydroxybenzyl)-benzothiazole-2-thione.

19. A composition according to claim 1 containing the compound 2,4-di(benzothiazol-2-thion-3-ylmethyl)-6-methylphenyl.

* * * * *